United States Patent

DuBois et al.

[11] Patent Number: 5,277,199
[45] Date of Patent: Jan. 11, 1994

[54] CORE WIRE STEERABLE CATHETERS

[75] Inventors: Thomas C. DuBois; George R. Foster, both of Glens Falls; Frank A. Bimbo, Queensbury, all of N.Y.

[73] Assignee: C. R. Bard, Inc., Murray Hill, N.J.

[21] Appl. No.: 927,868

[22] Filed: Aug. 10, 1992

Related U.S. Application Data

[63] Continuation of Ser. No. 583,528, Sep. 17, 1990, abandoned.

[51] Int. Cl.⁵ .............................................. A61B 5/00
[52] U.S. Cl. .................................. 128/772; 128/657; 604/283
[58] Field of Search .................. 128/657, 772; 604/95, 604/164, 280-

[56] References Cited

U.S. PATENT DOCUMENTS

| | | | |
|---|---|---|---|
| 3,995,623 | 12/1976 | Blake et al. | 128/2.06 E |
| 4,033,331 | 7/1977 | Guss et al. | 128/2 M |
| 4,582,181 | 4/1986 | Samson | 128/348.1 |
| 4,586,923 | 5/1986 | Gould et al. | 128/657 |
| 4,619,263 | 10/1986 | Frisbie et al. | 128/344 |
| 4,641,654 | 2/1987 | Samson et al. | 128/344 |
| 4,664,113 | 5/1987 | Frisbie et al. | 128/344 |
| 4,723,936 | 2/1988 | Buchbinder et al. | 128/657 |
| 4,771,778 | 9/1988 | Mar | 128/344 |
| 4,787,399 | 11/1988 | Bonello et al. | 128/657 |
| 4,875,481 | 10/1989 | Higgins | 128/344 |
| 4,955,384 | 9/1990 | Taylor et al. | 128/657 |

FOREIGN PATENT DOCUMENTS

0279958  8/1988  European Pat. Off. .

*Primary Examiner*—Max Hindenburg
*Attorney, Agent, or Firm*—Wolf, Greenfield & Sacks

[57] ABSTRACT

An improved and simplified catheter construction is provided to enhance the steerability of the catheter. The catheter(s) includes an elongate flexible relatively torsionally rigid core wire attached securely at each of the proximal and distal ends of the catheter. The core wire adds sufficient torsional rigidity to the catheter to enhance the steerability of the catheter when the catheter is manipulated from its proximal end by the physician. The catheter avoids the need for incorporating helically braided tubes in the wall of the catheter. The invention may be used to make a catheter having a reduced outer diameter or an increased inner luminal diameter.

8 Claims, 2 Drawing Sheets

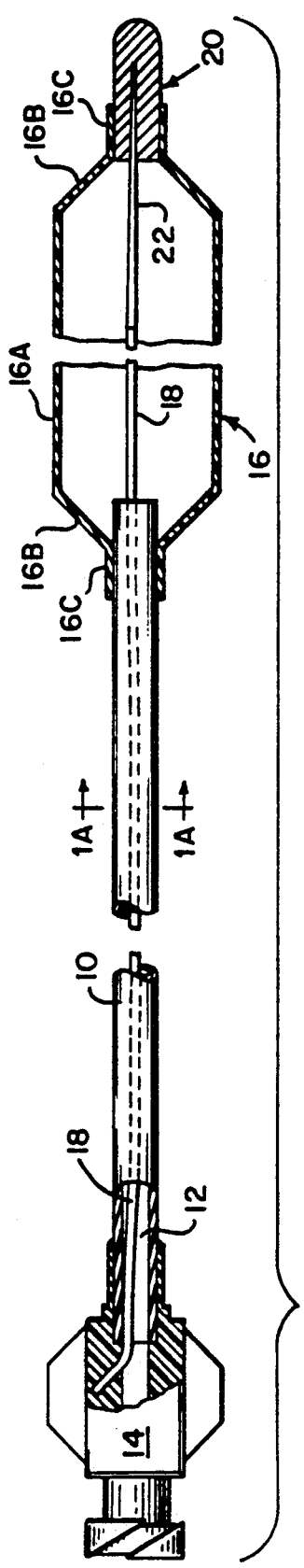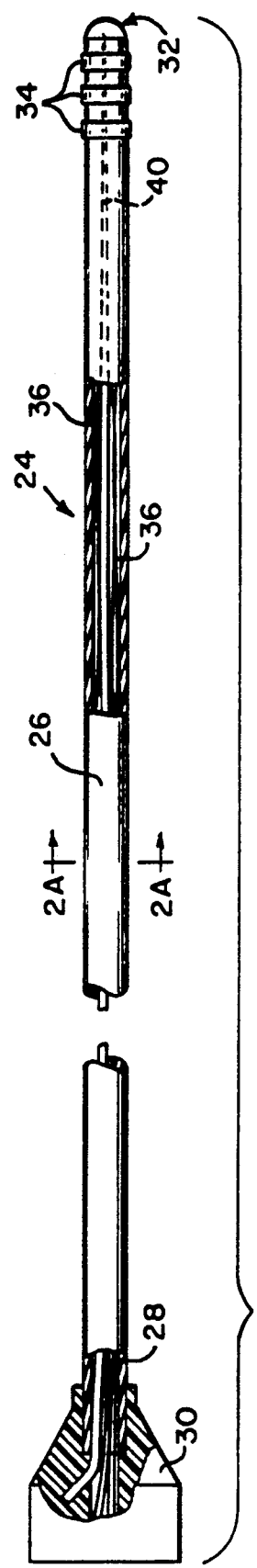

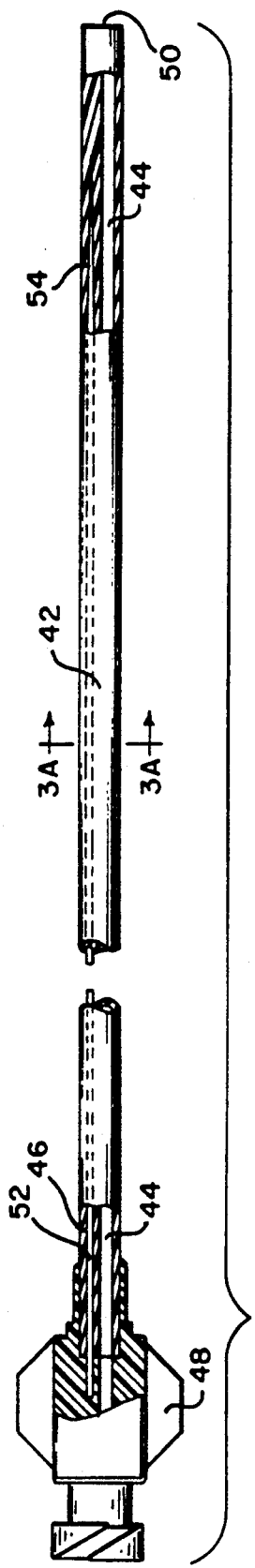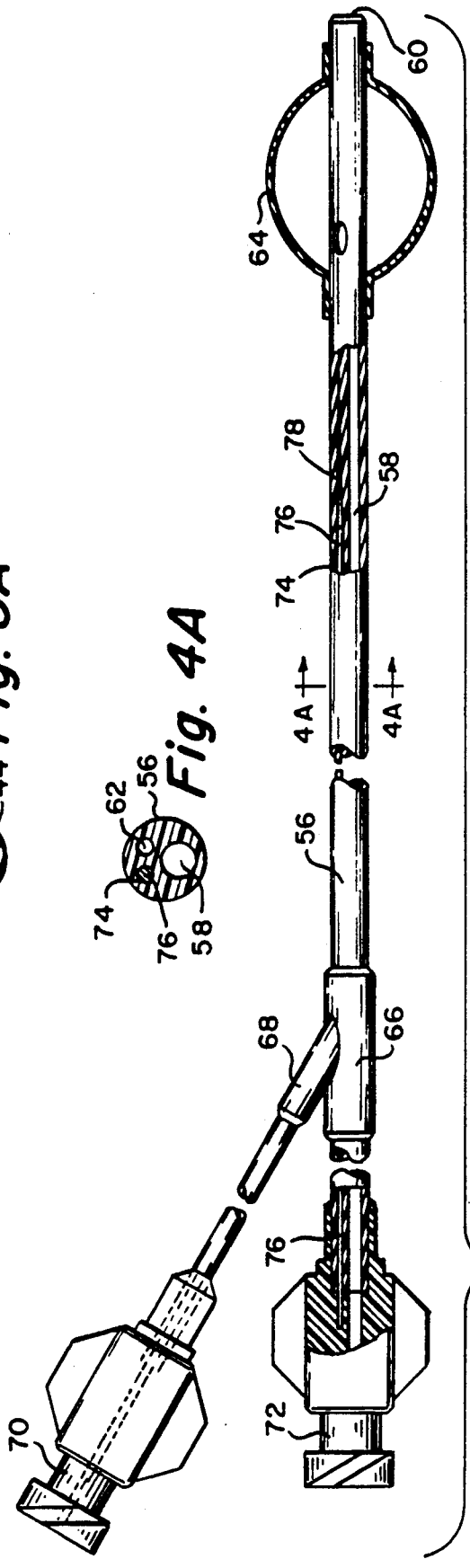

CORE WIRE STEERABLE CATHETERS

This application is a continuation, division, of application Ser. No. 07/583,528, filed Sep. 17, 1990 now abandoned.

FIELD OF THE INVENTION

This invention relates to improved constructions for steerable catheters.

BACKGROUND OF THE INVENTION

Of the wide variety of catheters used in the treatment and diagnosis of the human body, many require considerable manipulation and steering in order that the distal end of the catheter can reach the treatment site within the patient's body and perform its intended function. A few examples of such catheters include dilating catheters, electroprobes, angiographic catheters and flow directed catheters. Typically such catheters are provided with a curved distal end and have a shaft that is sufficiently torsionally rigid so that the distal end of the catheter can be caused to rotate by the physician rotating the catheter at its proximal end. In order to achieve such torsional rigidity, it often is the practice to build the tubular catheter in a plurality of sequential layers, one or more of which may be adapted to increase the torque transmission of the catheter from its proximal to its distal end. For example, in order to increase the torque transmission capability of a catheter it is common practice to incorporate a tubular braid of strong material such as stainless steel or a high strength polymer into the wall of the catheter, as one of its layers. Additionally, the configuration of the layers often is varied so as to vary the stiffness of the catheter along its length, particularly to make the catheter more flexible toward its distal end. Among the disadvantages of the layer by layer construction and of incorporating the braided tube into the wall of the catheter is that they are time consuming, labor intensive and expensive procedures. It would be desirable, therefore, to provide a less complex and less expensive construction for such catheters and it is among the principal objects of the present invention to provide such a construction.

SUMMARY OF THE INVENTION

Catheters made in accordance with the invention include an elongate flexible polymeric shaft having a proximal end and a distal end. A fitting is mounted on the proximal end for connection to a device, such as a syringe or an electrical connector or the like, depending on the intended purpose and function for the catheter. The distal end also is configured for the particular purpose for which the catheter is to be used, e.g., a balloon, electrode, open lumen or the like, as well as combinations thereof. In order to enhance the steerability of the catheter, a core wire extends the length of the catheter from its proximal fitting to the distal end. The core wire is sufficiently stiff to significantly enhance the torque transmission capability of the catheter. The core wire is attached at its proximal end to the fitting at the proximal end of the catheter and at its distal end, to the distal end of the catheter. The core wire may be embedded in the catheter wall or may be disposed in a lumen extending the length of the catheter The distal end of the core wire may be tapered to provide for progressively increasing flexibility of the catheter in the distal direction.

It is among the general objects of the invention to provide a simplified catheter construction in which the catheter has improved torque transmission characteristics.

It is also an object of the invention to provide a simplified catheter construction with progressively increasing flexibility in the distal direction.

A further object of the invention is to provide a catheter having excellent torque transmission property yet which avoids a multilayer labor intensive construction for the catheter.

Another object of the invention is to provide a catheter of the type described in which the use of tubular braids embedded in the catheter wall is avoided.

Yet another object of the invention is to provide a manufacturing technique and structure for a catheter which may be used in a wide variety of catheters.

DESCRIPTION OF THE DRAWINGS

The foregoing and other objects and advantages of the invention will be appreciated more fully from the following further description thereof, with reference to the accompanying drawings wherein:

FIG. 1 is a somewhat diagrammatic fragmented sectional illustration of a dilatation catheter incorporating the invention;

FIG. 1A is a cross sectional illustration of the shaft of the dilatation catheter as seen along the line 1A—1A of FIG. 1;

FIG. 2 is a somewhat diagrammatic fragmented sectional illustration of a steerable electroprobe incorporating the invention;

FIG. 2A is a cross sectional illustration of the steerable electrode probe of FIG. 2 as seen along line 2A—2A of FIG. 2;

FIG. 3 is a somewhat diagrammatic fragmented sectional illustration of a steerable angiographic catheter embodying the construction of the present invention;

FIG. 3A is a sectional illustration of the shaft of the catheter of FIG. 3 as seen along lines 3A—3A of FIG. 3;

FIG. 4 is a somewhat diagrammatic fragmented sectional illustration of a steerable flow directed catheter made in accordance with the invention; and FIG. 4A is a cross sectional illustration of the shaft of the catheter of FIG. 4 as seen along the line 4A—4A.

DESCRIPTION OF THE ILLUSTRATIVE EMBODIMENTS

FIG. 1 illustrates a catheter intended for use in dilatation of arteries, particularly peripheral arteries. The catheter includes an elongate flexible shaft 10 having a proximal end (to the left) and a distal end (to the right). The shaft 10 is formed from an appropriate polymeric material. For example, the shaft may be formed from a composite of nylon and polyether block amide (PEBAX TM) or any polyamide based elastomer. The catheter also may be formed to include different polymeric inner and outer layers, as in a coextrusion technique. For example, in a coextruded shaft the inner layer may be formed from a high lubricity material such as nylon and the outer material may be formed from a urethane material. In the embodiment of FIG. 1 the shaft 10 is formed to define an inner lumen 12. The catheter includes a luer fitting 14 attached to the proximal end of the shaft 10. A dilatation balloon 16 is mounted to the distal end of the shaft 10. The balloon 16 may be made as described in U.S. Pat. No. 4,490,421 to Levy, the disclosure of which is hereby incorporated by reference. The fitting 14 at the proximal end of the catheter is adapted to be connected to an inflation and deflation device (such as a syringe) by which the balloon 16 may be inflated and deflated through the lumen 12.

In order to enhance the torque transmission capability of the catheter, a core wire 18 is disposed within and extends the length of the lumen 12. The proximal end of the core wire is securely attached to the luer fitting 14 at the proximal end of the catheter with an appropriate adhesive, such as cyanoacrylate. The core wire also may be incorporated and integrally attached to the fitting by insert molding. The distal end of the core wire 18 protrudes distally beyond the end of the shaft 10 and terminates in an enlarged tip 20. The tip 20 may be molded from the same or similar polymeric material as that from which the shaft 10 is formed. The distal end of the core wire 18 extends through the balloon 16 and is secured to the tip 20. The balloon includes central cylindrical portion 16a, a pair of tapering cone sections 16b and a pair of cylindrical smaller diameter neck sections 16c that define the ends of the balloon 16. The balloon is attached to the catheter as by adhesively bonding the neck 16c at the proximal end of the balloon to the distal end of the catheter shaft 10 and by adhesively bonding the distal neck 16c to the catheter tip 20. A distal portion of the core wire 18 may be tapered, as indicated at 22 to provide the catheter with an increasing flexibility at its distal region.

In use, as the catheter is advanced through patients' blood vessels its distal end may be rotated and manipulated by rotation of the catheter at its proximal end by the fitting 14. Transmission of rotation from the proximal end to the distal end is enhanced by the core wire 18 which, together with the shaft 10 provides good torque transmission along the length of the catheter. Typically, a core wire 18 formed from stainless steel may be of the order of between 0.012" and 0.020" (approximately) in diameter in order to aid materially in the torque transmission for the catheter. The torque transmission is achieved in a relatively simple construction but without the requirement for the more labor intensive layer-by layer build up procedure and, in particular, without the requirement for incorporating a braided tube into the construction of the catheter wall. Progressively increased flexibility in the distal direction may also be achieved by a tapered core wire without the requirement of layer by-layer construction.

FIG. 2 illustrates another type of catheter incorporating the invention. The embodiment of FIG. 2 relates to a steerable electrode probe of the type that is intended to be inserted into a patient and manipulated into an intended body lumen, such as the region of the heart. The probe is intended to deliver electrical impulses to the internal site or alternately, to provide electrical sensing functions in order to monitor the electrical activity of the particular site in the body. The steerable electrode probe 24 of FIG. 2 includes an elongate flexible shaft 26 having an internal lumen 28 extending from its proximal to its distal end. Here, again, the shaft is formed from an appropriate polymeric material and may be extruded. A fitting, in the form of an electrical connector 30 is securely attached to the proximal end of the shaft. The distal end of the catheter has a closed tip 32. A number of ring electrodes 34 are mounted to the distal end of the catheter and are exposed exteriorly on the catheter shaft. The electrode rings 34 are connected to the connector 30 by insulated circuit wires 36 that extend through the lumen 28 of the catheter shaft 26. In accordance with the invention, the probe includes an elongate core wire 38 disposed within the lumen 28. The core wire 38 is attached at its proximal end to the connector 30 and at its distal end to the closed tip portion 32 of the catheter. As is the case with all the embodiments of the invention described herein, the core wire 38 is sufficiently torsionally rigid so that it may transmit torque from the proximal end to the distal end of the catheter. The distal portion of the core wire 38 preferably is tapered, as suggested, at 40. A probe so made will display a high degree of torque transmission but without requiring the labor intensive layer-by layer construction that has been typical of prior such catheters and probes. If the core wire is tapered, the probe will also display progressively increased flexibility in the distal direction. It is to be noted that with previous mapping probes, it has been common practice to incorporate a helical braid in the wall of the catheter in order to be able to transmit torque from the proximal to the distal end of the catheter. The inclusion of the braided layer necessarily results in a thicker wall than with the present invention. By omitting the braid, the present invention results in a catheter having a desirably lowered outer diameter and profile.

FIG. 3 illustrates another type of catheter with which the present invention may be used. This catheter, is intended to be used in angiographic applications, to deliver radiographic contrast liquid to a blood vessel to facilitate fluoroscopic visualization of the blood vessel. In this embodiment of the invention, the catheter is provided with an elongate flexible shaft 42 which may be extruded from an appropriate polymeric material. The shaft is formed to include two lumens, including a fluid lumen 44 through which radiographic contrast liquid may be injected, and a core wire lumen 46. A luer fitting 48 is securely attached to the proximal end of the shaft 42 and provides a means by which contrast liquid can be injected into the fluid lumen 44. The fluid lumen 44 is open at the distal tip of the shaft 42, terminating at tip and side hole orifices 50. The core wire lumen 46 which contains a core wire 52 is contained within the wall of the shaft 42 so as to maximize the cross sectional flow area of the fluid lumen 44. In angiographic catheters it is important that the catheter be able to deliver a relatively large volume of radiographic contrast liquid. A larger fluid lumen 44, therefore, is desirable.

It is desirable in angiographic catheters to be able to deliver a maximum volume of radiopaque contrast liquid in a short time, the catheter being intended to accommodate high flow rates. High flow rates of radiopaque contrast liquids are important in order that the blood vessel or other body lumen being investigated is fully and effectively filled with a high concentration of radiopaque contrast liquid which will be highly visible under X ray fluoroscopy. By using the present invention, the cross sectional flow area of the fluid lumen may be maximized. By using a core wire as in the present invention, it is unnecessary to use a torque transmitting braid in the wall of the catheter. As a result, the wall may be thinner which provides capability for increasing the cross sectional area of the fluid lumen 44. As in the previously described embodiments, the core wire 52 is secured at its proximal end to the luer fitting 48. The distal end of the core wire, which may be tapered as indicated at 54, also is secured within the wall of the catheter as by adhesive. Additionally, if the core wire is tapered, it is possible to provide progressively increased flexibility in the distal direction without requiring a layer by-layer construction.

In order to attach securely the core wire within its lumen, the lumen 46 may be formed to be slightly larger in diameter, for example, about 0.001", than the diameter of the core wire to enable the core wire to be slipped into the lumen. Before inserting the core wire into the lumen, the lumen may be filled with an adhesive. A small temporary hole may be formed through the side wall of the catheter in communication with the distal end of the lumen 46 either to enable air to escape when adhesive is injected into the lumen from its proximal end or to enable adhesive to be injected directly into the distal end of the lumen through the side hole. Alternately, the core wire may be attached securely within its lumen without the use of a separate adhesive by heating the catheter while the core wire is in place to a degree sufficient to cause the inner surface of the core wire lumen to become tacky and adhere to the core wire. During such heat bonding a mandrel should be inserted through other lumen(s) of the catheter to assure their integrity.

FIG. 4 shows another type of catheter incorporating the present invention in the form of a steerable flow directed catheter. A flow directed catheter typically is provided with a balloon at the distal end and it is the purpose of the balloon to be carried with the blood flow to the desired location in the blood vessel. As shown in FIG. 4, this embodiment of the catheter includes an elongate flexible shaft 56 that may be formed from an extruded polymeric material. The shaft typically will include a relatively large diameter fluid lumen 58 that extends the length of the shaft 56 and terminates in outlet orifices 60 at the distal part of the shaft. The shaft 56 also includes an inflation lumen 62 (FIG. 4A) which extends from the proximal end of the catheter t the distal end and terminates at its distal end in communication with the interior of a balloon 64. The balloon 64 is attached to the catheter shaft as by adhesive. The balloon for such a catheter typically may be formed from latex. A Y-fitting 66 is mounted to the shaft in the region of its proximal end and includes an inflation leg 68 which terminates in a luer fitting 70. The luer fitting 70 is intended to be connected to an inflation and deflation device, such as a syringe (not shown) to inflate and deflate the balloon 64. The proximal end of the main shaft terminates in another luer fitting 72 which is securely attached to the proximal end of the shaft 56. The shaft 56 also includes a core wire lumen 74 that extends from the proximal end of the shaft toward the distal end. The core wire lumen 74 receives a core wire 76. The proximal end of the core wire is securely attached to the luer fitting 72. The distal end of the core wire 76, which may be tapered as indicated at 78 is attached securely to the distal portion of the catheter shaft as described above.

As with the previously described embodiments, the catheter benefits from the present invention by incorporating a core wire to impart torsional rigidity to the catheter in that it omits the need for braids and the like, thereby resulting in a thinner wall for the catheter. The core wire also can provide progressively increased flexibility in the distal direction without the requirement of changing the configuration of layers of material.

From the foregoing it will be appreciated that the invention provides a simple, yet effective, means for enhancing the torque transmission capabilities of a wide variety of catheters. It also provides a means to vary the flexibility of the catheter by a simple construction. In particular, it also provides a simplified technique for manufacture that is less labor intensive and less costly than with prior techniques. The invention avoids the use of torque transmitting braids and the like.

The foregoing embodiments have been illustrated, for convenience, without curves at the distal end of the catheters. It may be desirable to form an appropriate curve in the distal end of catheters incorporating the present invention in order to facilitate steerability of the catheter.

It should be understood, however, that the foregoing description of the invention is intended merely to be illustrative thereof and that other embodiments, modifications and equivalents may be apparent to those skilled in the art without departing from the spirit.

Having thus described the invention what I desire to claim and secure by Letters Patent is:

1. A catheter adapted to transmit rotation from its proximal end to its distal end comprising:
    an elongate flexible shaft having at least one lumen formed therethrough;
    a fitting rigidly and non-rotatably attached to the proximal end of the shaft; and
    a core wire extending through said at least one lumen, the core wire being attached rigidly and non-rotatably at its proximal end to the fitting and attached at its distal end to a more distal portion of the catheter.

2. A catheter as defined in claim 1 wherein the distal portion of the core wire is tapered thereby to define a configuration of increasing flexibility in a distal direction.

3. A catheter as defined in either of claims 1 or 2 further comprising:
    a balloon mounted to the distal end of the catheter;
    an inflation lumen extending through the shaft, the distal end of the inflation lumen being in communication with the interior of the balloon, the proximal end of the inflation lumen being in communication with the fitting;
    the core wire extending through the inflation lumen and the balloon;
    a tip member disposed at the distal tip of the catheter; and
    the core wire and balloon being attached, at their distal ends, to the tip member and to each other.

4. A catheter as defined in either of claims 1 or 2 wherein said catheter comprises an electrode probe further comprising:
    said proximal fitting being a connector;
    the lumen extending through the catheter being closed at its distal end in a tip element;
    the core wire being attached at its proximal end to the fitting and at its distal end to the closed distal element of the catheter;
    the electrode means mounted to the distal end of the catheter and exposed outwardly thereof; and
    conductor means extending through the lumen and being connected at one end to the connector and at the other end to the electrodes.

5. The catheter as defined in either of claims 1 or 2 wherein the catheter comprises an angiographic catheter and, further comprising:
    a through lumen extending from the proximal fitting to the distal end of the shaft and opening at more distal outlet openings; and the core wire terminating short of or at the distal end of the catheter, the core wire being embedded in a separate core wire lumen formed in the catheter wall, a distal part of the core wire being securely attached to the wall.

6. A catheter as defined in claims 1 or 2 wherein the catheter comprises a flow directed catheter, further comprising:

a flow direction balloon mounted to the distal end of the catheter;

an inflation lumen extending through the catheter and having a distal end in communication with the interior of the balloon, while the proximal end of the inflation lumen extends through a "Y" fitting and inflation leg and terminating in a fitting;

the catheter shaft further having a through lumen extending from the first mentioned fitting to the distal part of the catheter and opening at the distal part in distal outlet orifices; and the core wire lumen terminating short of or at the distal end of the catheter shaft and being secured thereto.

7. A catheter as defined in claim 1 wherein the proximal end of the core wire is attached to the fitting with an adhesive.

8. A catheter as defined in claim 1 wherein the proximal end of the core wire is integrally attached to the fitting by inserting molding.

* * * * *